United States Patent
Steffan et al.

(10) Patent No.: US 9,822,051 B2
(45) Date of Patent: Nov. 21, 2017

(54) METHOD FOR PRODUCING ACROLEIN

(71) Applicants: Martin Steffan, Singapore (SG); Helmut Mueller, Jossgrund (DE); Philipp Roth, Hanau (DE); Christoph Weckbecker, Gruendau (DE); Harald Jakob, Hasselroth (DE)

(72) Inventors: Martin Steffan, Singapore (SG); Helmut Mueller, Jossgrund (DE); Philipp Roth, Hanau (DE); Christoph Weckbecker, Gruendau (DE); Harald Jakob, Hasselroth (DE)

(73) Assignee: Evonik Degussa GmbH, Essen (DE)

(*) Notice: Subject to any disclaimer, the term of this patent is extended or adjusted under 35 U.S.C. 154(b) by 0 days.

(21) Appl. No.: 14/894,752

(22) PCT Filed: May 23, 2014

(86) PCT No.: PCT/EP2014/060717
§ 371 (c)(1),
(2) Date: Nov. 30, 2015

(87) PCT Pub. No.: WO2014/195157
PCT Pub. Date: Dec. 11, 2014

(65) Prior Publication Data
US 2016/0107968 A1    Apr. 21, 2016

Related U.S. Application Data

(60) Provisional application No. 61/830,459, filed on Jun. 3, 2013.

(30) Foreign Application Priority Data

Jun. 3, 2013 (EP) .................... 13170210

(51) Int. Cl.
| | | |
|---|---|---|
| C07C 45/35 | (2006.01) | |
| C07C 51/00 | (2006.01) | |
| C07C 51/235 | (2006.01) | |
| B01J 23/888 | (2006.01) | |
| B01J 23/889 | (2006.01) | |
| B01J 23/89 | (2006.01) | |
| C07C 51/25 | (2006.01) | |

(52) U.S. Cl.
CPC .......... *C07C 45/35* (2013.01); *B01J 23/8885* (2013.01); *B01J 23/8898* (2013.01); *B01J 23/8993* (2013.01); *C07C 51/235* (2013.01); *C07C 51/252* (2013.01)

(58) Field of Classification Search
CPC ............................ C07C 45/35; C07C 51/25
USPC .................... 568/477, 479, 480; 562/532
See application file for complete search history.

(56) References Cited

U.S. PATENT DOCUMENTS

| | | |
|---|---|---|
| 3,009,960 A | 11/1961 | Shotts et al. |
| 6,545,178 B1 | 4/2003 | Tanimoto et al. |
| 7,119,233 B2 | 10/2006 | Duebner et al. |
| 7,402,705 B2 | 7/2008 | Redlingshoefer et al. |
| 7,498,454 B2 | 3/2009 | Redlingshoefer et al. |
| 7,790,934 B2 | 9/2010 | Redlingshoefer et al. |
| 7,846,861 B2 | 12/2010 | Redlingshoefer et al. |
| 8,008,227 B2 | 8/2011 | Fischer et al. |
| 8,222,461 B2 | 7/2012 | Fischer et al. |
| 8,772,551 B2 | 7/2014 | Fischer et al. |
| 9,156,782 B2 | 10/2015 | Koerfer et al. |
| 2004/0015011 A1 | 1/2004 | Krokoszinski et al. |
| 2009/0018362 A1 | 1/2009 | Dubois |
| 2016/0068480 A1 | 3/2016 | Koerfer et al. |

FOREIGN PATENT DOCUMENTS

| | | |
|---|---|---|
| EP | 0 959 062 B1 | 7/2003 |
| EP | 1 981 835 A2 | 10/2008 |
| WO | WO 02/00587 A1 | 1/2002 |
| WO | WO 2007/090991 A2 | 8/2007 |
| WO | WO 2007/090991 A3 | 8/2007 |

OTHER PUBLICATIONS

International Search Report issued Jul. 24, 2014, in PCT/EP2014/060717 filed May 23, 2014.

*Primary Examiner* — Sikarl Witherspoon
(74) *Attorney, Agent, or Firm* — Oblon, McClelland, Maier & Neustadt, L.L.P.

(57) ABSTRACT

The present invention relates to a process for preparing acrolein from propylene by catalytic gas phase oxidation with molecular oxygen (for example air). The invention further relates to the use of particular propylene-containing starting materials, for example refinery grade propylene, for preparation of acrolein.

17 Claims, No Drawings

METHOD FOR PRODUCING ACROLEIN

The present invention relates to a process for preparing acrolein from propylene by catalytic gas phase oxidation with molecular oxygen (for example air). The invention further relates to the use of particular propylene-containing starting materials, for example refinery grade propylene, for preparation of acrolein.

Acrolein is used as an intermediate in the industrial scale preparation of the synthetic amino acid DL-methionine and the hydroxy analogue thereof DL-2-hydroxy-4-methylmercaptobutyric acid, which are of considerable economic significance as a feed mix constituent in animal nutrition.

Industrial preparation in the chemical industry is effected very substantially via gas phase oxidation of propane or propylene in the presence of suitable heterogeneous catalysts. This partial oxidation is effected with air as the oxidizing agent at temperatures in the range of about 300 to 400° C., using, for example, tube bundle reactors in which the strongly exothermic reaction is cooled with salt baths. Only a relatively dilute mixture of propylene with air (usually also in the presence of steam) is used, in order to avoid the formation of explosive mixtures. The yields of acrolein achievable with modern catalysts are about 83 to 90% based on propylene (Ullmanns Encyclopedia of Industrial Chemistry, "Acrolein and Methacrolein"); by-products formed are 5 to 10% acrylic acid and 3 to 6% carbon monoxide and carbon dioxide, as well as unconverted propylene.

As well as these, further secondary components are also known, as described, for example in U.S. Pat. No. 6,057,481 and DT 1618889. These include acetaldehyde, formaldehyde, organic acids (e.g. acetic acid), ketones and water.

The occurrence of secondary components depends not only on unselective reactions of the propylene over the catalyst but also strongly on impurities in the propylene used. Propylene is generally obtainable in three qualities which differ by the propylene content, this typically being more than 99.1% for polymer grade, in the range from 92 to 96% for chemical grade and between 50 and 70% for refinery grade (Process Economics Program Report 267, "PROPYLENE PRODUCTION", October 2008). The main secondary component is propane, but also higher saturated and unsaturated hydrocarbons, and also sulphur compounds, as described in Table 4.9 of the aforementioned report.

It is likewise stated that refinery grade propylene can be used directly for certain chemical operations, for example in the preparation of cumene or isopropanol. It is mentioned, however, that the concentration of sulphur should not be greater than about 2 ppm (cf. Table 3.2 in Process Economics Program Report 267, "PROPYLENE PRODUCTION", October 2008). This agrees with the patent application US 2004/0192986 A1 to Wu et al., which states that the removal of sulphur components from olefinic hydrocarbon streams leads to an increase in the service life and efficiency of the catalysts in cumene synthesis.

EP 09 595 062 B1 states that saturated hydrocarbons such as propane have only a low reactivity with the catalyst in the conversion of propylene to acrolein (and subsequently to acrylic acid) and thus exert only a low level of influence on the catalyst performance and catalyst service life. What is critical, however, is the presence of unsaturated hydrocarbons in the propylene feed, since they can react with the catalyst under the prevailing conditions and thus lead to by-products, and can worsen the catalyst performance.

It has now been found that, surprisingly, in the preparation of acrolein by catalytic gas phase oxidation of propylene with molecular oxygen, it is possible to employ propylene gas of lower quality without significantly worsening the performance characteristics of the oxidation catalyst used compared to the use of high-quality propylene. It was expected that the yield of acrolein would decline over a prolonged period of operation in the case of use of sulphur components, since side reactions can be enabled by the sulphur compound in the reaction system, or the catalyst is poisoned and selectivity for acrolein thus decreases. More particularly, it has been found that the propylene used, or a propylene-containing reaction gas, may contain sulphur and/or unsaturated hydrocarbons without any significant deterioration in the conversion of propylene and the yield of acrolein compared to the use of propylene without the impurities mentioned.

In addition, refinery grade propylene (75.48% by weight of propylene, 24.04% by weight of propane, 0.28% by weight of ethane, remainder saturated and unsaturated C2 to C5 hydrocarbons (excluding $C_3$ and ethane), 0.7 mg/kg of sulphur, water content below 20 mg/kg) was used as a feed gas for the partial oxidation in the presence of molecular oxygen over a mixed oxide catalyst as described in DE 10 2006 015710 A1. Analogously to the experiments with sulphur component, no significant influence on catalyst performance was found.

The propane present in refinery grade propylene can also be used advantageously firstly as an inert gas (under the conditions described above), and secondly as a fuel gas in a thermal post-combustion connected downstream of the process, which in turn allows a saving of methane, which is typically used as the fuel gas.

The present invention provides a process for preparing acrolein by catalytic gas phase oxidation, said process comprising the following steps:

a) providing a reaction gas comprising propylene and molecular oxygen, and b) contacting the reaction gas with an oxidation catalyst to form a gas mixture comprising acrolein, the oxidation catalyst being a mixed oxide catalyst comprising or consisting of one or more base components selected from molybdenum, vanadium and tungsten, characterized in that more than 10 ppm by weight of sulphur in the form of any sulphur components is present in the reaction gas provided, but not more than 5000 ppm by weight of sulphur in the form of any sulphur components and not more than 5000 ppm by weight of unsaturated hydrocarbons selected from the group consisting of $C_2H_4$, $C_3H_4$, $C_4H_8$, $C_4H_6$, $C_5H_{10}$, $C_5H_8$ and mixtures thereof is present in each case in the reaction gas provided.

The content of sulphur (in the form of any sulphur components) in the reaction gas provided is determined in accordance with standard EN 24 260 (combustion according to Wickbold). The content of unsaturated hydrocarbons selected from the group consisting of $C_2H_4$, $C_3H_4$, $C_4H_8$, $C_4H_6$, $C_5H_{10}$, $C_5H_8$ and mixtures thereof in the reaction gas provided is determined by standard DIN 51619 (gas chromatography). If alternative variants of the procedures are mentioned in the standards, the above-specified ppm by weight values have to be achieved by at least one of the possible alternative variants.

The process according to the invention also allows more than 50 ppm by weight of unsaturated hydrocarbons selected from the group consisting of $C_2H_4$, $C_3H_4$, $C_4H_8$, $C_4H_6$, $C_5H_{10}$, $C_5H_8$ and mixtures thereof to be additionally present in the reaction gas provided.

Unsaturated hydrocarbons selected from the group consisting of $C_2H_4$, $C_3H_4$, $C_4H_8$, $C_4H_6$, $C_5H_{10}$, $C_5H_8$ and mixtures thereof, mean especially ethene, propadiene, methylacetylene, isobutene, 1-butene, cis-2-butene, trans-2-butene, butadiene, 1-pentene and mixtures thereof.

In the process according to the invention, the total content of sulphur in the form of any sulphur components in the reaction gas provided may also be more than 20 ppm by weight. It is preferable, however, when the total content of sulphur is not more than 1000 ppm by weight.

More particularly, the process according to the invention allows the total content of sulphur in the form of $H_2S$ and/or $SO_2$ in the reaction gas provided to be more than 20 ppm by weight or else more than 30 ppm by weight or more than 40 ppm by weight, provided that the total content of sulphur in the form of any sulphur components (including $H_2S$ and/or $SO_2$) in the starting material is preferably not more than 1000 ppm by weight, more preferably not more than 500 ppm by weight, and especially preferably not more than 250 ppm by weight.

More particularly, the process according to the invention also allows the total content of unsaturated hydrocarbons, selected from the group consisting of $C_2H_4$, $C_3H_4$, $C_4H_8$, $C_4H_6$, $C_5H_{10}$, $C_5H_8$ and mixtures thereof, in the reaction gas provided to be more than 100 ppm by weight or else more than 150 ppm by weight or more than 200 ppm by weight, but not more than 1500 ppm by weight, preferably not more than 1300 ppm by weight, and more preferably not more than 1000 ppm by weight.

In a preferred embodiment of the process according to the invention, the mixed oxide catalyst additionally contains one or more additional components selected from bismuth, antimony, tellurium, tin, iron, cobalt, nickel and copper.

Particularly suitable oxidation catalysts in the context of the present invention are selected from mixed oxide catalysts of the general formula (I) or mixtures of various mixed oxide catalysts of the general formula (I) where:

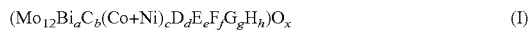

$$(Mo_{12}Bi_aC_b(Co+Ni)_cD_dE_eF_fG_gH_h)O_x \quad (I)$$

C=iron,
D=at least one of the elements from W, P,
E=at least one of the elements from Li, K, Na, Rb, Cs, Mg, Ca, Ba, Sr,
F=at least one of the elements from Ce, Mn, Cr, V,
G=at least one of the elements from Nb, Se, Te, Sm, Gd, La, Y, Pd, Pt, Ru, Ag, Au,
H=at least one of the elements from Si, Al, Ti, Zr,
a=0 to 5.0,
b=0.5 to 5.0,
c=2 to 15,
d=0.01 to 5.0,
e=0.001 to 2,
f=0.001 to 5,
g=0 to 1.5,
h=0 to 800,
x=number which is determined by the valency and frequency of the elements other than oxygen.

As already explained, one advantage of the process according to the invention is that, in the preparation of acrolein by catalytic gas phase oxidation of propylene, it is possible to employ propylene gas of lower quality without significantly worsening the performance characteristics of the oxidation catalyst used compared to the use of propylene of high quality. As described above, this is especially true of contamination by sulphur components and/or unsaturated hydrocarbons ($C_2$-$C_5$), excluding $C_3$.

However, the process according to the invention also allows the reaction gas provided to be produced by mixing at least refinery grade propylene and air, the refinery grade propylene being characterized in that it contains 0.05 to 2.0% by weight, preferably 0.1 to 1.0% by weight and further preferably 0.2 to 0.5% by weight of ethane and/or 9 to 40% by weight, preferably 10 to 35% by weight, further preferably 12 to 30% by weight, and especially preferably 15 to 25% by weight of propane.

The process according to the invention is preferably performed in such a way that, in step b), the reaction gas is passed through a reactor tube or through a plurality of bundled reactor tubes in parallel, the one or more reactor tubes each being filled with the oxidation catalyst to a length of at least 2 meters, preferably at least 2.5 meters, more preferably at least 3 meters. Typically, the reactor tubes are each charged with oxidation catalyst to a length of 1.5 to 5 meters, preferably 2 to 4.5 meters, more preferably 2.5 to 4 meters. The internal diameter of each reactor tube is in the range from 1.0 to 3.5 cm, preferably in the range from 1.5 to 3.3 cm, more preferably in the range from 2.0 to 3.0 cm.

In addition, the process according to the invention is preferably performed in such a way that, in step b), the reaction gas is passed through the reactor tube or the plurality of reactor tubes in a bundle at a temperature in the range from 300 to 500° C., preferably in the range from 350 to 450° C., more preferably in the range from 370 to 430° C. The temperature can be set by controlling the temperature of the one or more reactor tube(s), for example by surrounding the one or more reactor tube(s) with a temperature-controlled heat carrier medium or by direct heating of the one or more reactor tube(s) with electrical heating elements.

It has been found that step b) of the process according to the invention can be operated over a period of 30 minutes to 2000 hours, preferably in the range from 1 to 1000 hours, more preferably in the range from 2 to 500 hours, without occurrence of any significant deterioration in the performance characteristics of the oxidation catalyst used; in this context, only the periods within which the reaction gas actually contains the amounts of sulphur components and/or unsaturated hydrocarbons specified in accordance with the invention are added up.

The present invention further provides for the use of a reaction gas for preparation of acrolein, characterized in that the reaction gas contains more than 10 ppm by weight of sulphur in the form of any sulphur components, the reaction gas in each case containing not more than 5000 ppm by weight, preferably not more than 1000 ppm by weight, of sulphur in the form of any sulphur components and not more than 5000 ppm by weight, preferably not more than 1500 ppm by weight, of unsaturated hydrocarbons, selected from the group consisting of $C_2H_4$, $C_3H_4$, $C_4H_8$, $C_4H_6$, $C_5H_{10}$, $C_5H_8$ and mixtures thereof.

The process according to the invention also allows more than 50 ppm by weight of unsaturated hydrocarbons selected from the group consisting of $C_2H_4$, $C_3H_4$, $C_4H_8$, $C_4H_6$, $C_5H_{10}$, $C_5H_8$ and mixtures thereof to be present in the reaction gas provided.

The total content of sulphur in the form of any sulphur components and/or of unsaturated hydrocarbons, selected from the group consisting of $C_2H_4$, $C_3H_4$, $C_4H_8$, $C_4H_6$, $C_5H_{10}$, $C_5H_8$ and mixtures thereof, in the reaction gas may also be more than 20 ppm by weight in each case. More particularly, the inventive use allows the total content of sulphur in the form of $H_2S$ and/or $SO_2$ in the reaction gas to be more than 10 ppm by weight or else more than 20 ppm by weight, provided that the total content of sulphur in the form of any sulphur components (including $H_2S$ and/or $SO_2$) in the reaction gas is not more than 5000 ppm by weight, preferably not more than 1000 ppm by weight.

The present invention further also provides for the use of an acrolein-containing gas mixture which is preparable by the process described above for preparation of acrylic acid.

In a preferred embodiment of the inventive use, the preparation of acrylic acid comprises the mixing of the acrolein-containing gas mixture with further molecular oxygen and the contacting of the mixture with an oxidation catalyst to form an acrylic acid-containing gas mixture. This can be effected without purifying removal of any sulphur present in the form of any sulphur components and of any unsaturated hydrocarbons selected from the group consisting of $C_2H_4$, $C_4H_8$, $C_3H_4$, $C_4H_6$, $C_5H_{10}$, $C_5H_8$ and mixtures thereof that are present.

EXAMPLES

Example 1

In a tubular reactor with 20 ml of catalyst bed, the heterogeneously catalysed partial oxidation of propylene was performed in the presence of molecular oxygen over a mixed metal oxide catalyst, the preparation method for which can be found in DE 10 2006 015710 A1 (Example 1). As well as propylene and air, nitrogen (and optionally steam) was fed in as additional inert gas. The reactor was heated to about 360° C. by means of an electrical oven. The temperature in the catalyst bed was monitored by means of thermocouples, and the maximum temperature was about 400° C. The analysis of the process gas was performed by means of gas chromatography.

The reaction was first started up under standard conditions (=feed gas consisting of propylene, oxygen and inert gas, e.g. nitrogen). In order to study the influence of sulphur components, a mixture of sulphur component in inert gas (e.g. $H_2S$ in nitrogen) was metered in by means of an additional mass flow meter and replaces the inert gas of the standard conditions in a parallel stepwise manner, such that the total volume flow rate was kept constant. Results are given hereinafter according to various catalyst run times and the respective proportion by mass of sulphur component (based on the overall gas stream):

TABLE 1

Catalyst performance after various run times with and without metered addition of $H_2S$.

| Run time [h] | Proportion by mass of $H_2S$ [34 g/mol] [ppm by wt.] | Proportion by mass of sulphur [32 g/mol] [ppm by wt.] | $H_2S$ metering time [h] | Propylene conversion [%] | Acrolein yield [%] |
|---|---|---|---|---|---|
| 50 | 0 | 0 | — | 90.1 | 80.0 |
| 135 | 0 | 0 | — | 90.6 | 80.0 |
| 315 | 220 | 207 | 150 | 91.6 | 80.1 |
| 550 | 435 | 409 | 337 | 89.9 | 80.0 |
| 810 | 870 | 819 | 260 | 90.0 | 80.6 |
| 1080 | 1500 | 1412 | 103 | 91.3 | 80.9 |

Example 2

A bed of 2850 mm of catalyst was introduced into a tubular reactor of length 3400 mm with internal diameter of 21.7 mm. The reactor is surrounded by a heat carrier medium and thus kept at a constant temperature of 350° C. The reactor was charged with a reaction gas composed of propylene (9.3% by weight), air (58.3% by weight), remainder inert gas. Via a separate control path, $SO_2$ (as a pure substance and/or as a mixture with inert gas) was first metered in. The catalyst was run in and the metered addition of the sulphur component was commenced only after several days of steady-state operation. The proportion by mass was then increased gradually.

TABLE 2

Catalyst performance after various run times without and with metered addition of $SO_2$ or $H_2S$.

| Run time [h] | Proportion by mass of $SO_2$ [64 g/mol] [ppm by wt.] | Proportion by mass of Sulphur [32 g/mol] [ppm by wt.] | $SO_2$ metering time [h] | Propylene conversion [%] | Acrolein yield [%] |
|---|---|---|---|---|---|
| 50 | 0 | 0 | — | 97.6 | 85.6 |
| 150 | 0 | 0 | — | 97.5 | 85.6 |
| 350 | 0 | 0 | — | 97.6 | 85.4 |
| 660 | 250 | 125 | 288 | 97.4 | 85.2 |
| 1000 | 1000 | 500 | 72 | 98.3 | 85.9 |
| 1200 | 2000 | 1000 | 120 | 98.7 | 85.9 |
| 1440 | 5000 | 2500 | 72 | 97.2 | 85.3 |
| 1670 | 10000 | 5000 | 120 | 97.5 | 79.8 |

| Regeneration ||||||
|---|---|---|---|---|---|
| Run time [h] | Proportion by mass of $SO_2$ [ppm by wt.] | Proportion by mass of Sulphur [ppm by wt.] | $SO_2$ metering time [h] | Propylene conversion [%] | Acrolein yield [%] |
| 1800 | 500 | 250 | 72 | 97.5 | 85.2 |
| 1950 | 1000 | 500 | 72 | 97.6 | 84.7 |

The results (conversion, yield) up to a catalyst run time of 350 h, in which no sulphur component was metered in, show the performance of the catalyst without involvement of sulphur components.

The run times reported in Tables 1 and 2 are gross run times. The period of $H_2S$ or $SO_2$ metering with a particular proportion by mass of $H_2S$ or $SO_2$ reported in each case took place within the period between the run times of $H_2S$ or $SO_2$ metering with the next highest or next lowest proportion by mass of $H_2S$ or $SO_2$.

Example: The period of $SO_2$ metering of 288 h at a proportion by mass of $SO_2$ of 250 ppm by weight was within the interval between run time 350 and 1000 h.

For the rest of the interval, reaction gas was passed through the tubular reactor without $SO_2$ metering.

The invention claimed is:

1. A process for preparing acrolein by catalytic gas phase oxidation, the process comprising:
   a) providing a reaction gas comprising propylene and molecular oxygen, and
   b) contacting the reaction gas with an oxidation catalyst to form a gas mixture comprising acrolein, wherein the oxidation catalyst is a mixed oxide catalyst comprising at least one base component selected from the group consisting of molybdenum, vanadium, and tungsten, wherein the reaction gas is passed through a reactor tube or a plurality of reactor tubes in a bundle at a temperature of from 350° C. to 450° C.,
   wherein the reaction gas comprises from 250 ppm to 5000 ppm by weight of sulphur in the form of a sulphur component and not more than 5000 ppm by weight of at last one unsaturated hydrocarbon selected from the group consisting of $C_2H_4$, $C_3H_4$, $C_4H_8$, $C_4H_6$, $C_5H_{10}$, and $C_5H_8$, wherein the reaction gas is passed through a reactor tube or a plurality of bundled reactor tubes in parallel, and the reactor tube or the plurality of bundled reactor tubes are filled with the oxidation catalyst to a length of at least 2 meters.

2. The process according to claim 1, wherein the reaction gas comprises more than 50 ppm by weight of the at least one unsaturated hydrocarbon selected from the group consisting of $C_2H_4$, $C_3H_4$, $C_4H_8$, $C_4H_6$, $C_5H_{10}$, and $C_5H8$.

3. The process according to claim 1, wherein the reaction gas comprises from more than 250 ppm by weight to 1000 ppm by weight of sulphur in the form of a sulphur component.

4. The process according to claim 1, wherein the reaction gas comprises from more than 250 ppm to 1000 ppm by weight of sulphur in the form of $H_2S$ and/or $SO_2$.

5. The process according to claim 1, wherein the reaction gas comprises from more than 100 ppm to 1500 ppm by weight of the at least one unsaturated hydrocarbon selected from the group consisting of $C_2H_4$, $C_3H_4$, $C_4H_8$, $C_4H_6$, $C_5H_{10}$, and $C_5H8$.

6. The process according to claim 1, wherein the reaction gas comprises from more than 150 ppm to 1300 ppm by weight of the at least one unsaturated hydrocarbon selected from the group consisting of $C_2H_4$, $C_3H_4$, $C_4H_8$, $C_4H_6$, $C_5H_{10}$, and $C_5H8$.

7. The process according to claim 1, wherein the mixed oxide catalyst further comprises at least one additional component selected from the group consisting of bismuth, antimony, tellurium, tin, iron, cobalt, nickel and copper.

8. The process according to claim 7, wherein the oxidation catalyst is a mixed oxide catalyst of the formula (I) or a mixture of various mixed oxide catalysts of the formula (I):

$$(Mo_{12}Bi_aC_b(Co+Ni)_cD_dE_eF_fG_gH_h)O_x \quad (I),$$

C=iron,
D=at least one of the elements from W, P,
E=at least one of the elements from Li, K, Na, Rb, Cs, Mg, Ca, Ba, Sr,
F=at least one of the elements from Ce, Mn, Cr, V,
G=at least one of the elements from Nb, Se, Te, Sm, Gd, La, Y, Pd, Pt, Ru, Ag, Au,
H=at least one of the elements from Si, Al, Ti, Zr,
a=0 to 5.0,
b=0.5 to 5.0,
c=2 to 15,
d=0.01 to 5.0,
e=0.001 to 2,
f=0.001 to 5,
g=0 to 1.5,
h=0 to 800, and
x=number which is determined by the valency and frequency of elements other than oxygen.

9. The process according to claim 1, wherein the reaction gas is produced by mixing at least refinery grade propylene and air, wherein the refinery grade propylene comprises from 0.05 to 2.0% by weight of ethane and/or from 9 to 40% by weight of propane.

10. The process according to claim 1, wherein the reaction gas is passed through a reactor tube or a plurality of reactor tubes in a bundle at a temperature of from 370° C. to 430° C.

11. The process according to claim 1, wherein the reactor tubes are charged with oxidation catalyst to the length of at least 3 meters.

12. The process according to claim 1, wherein the length the reactor tubes are charged with oxidation catalyst to the length of 1.5 to 5 meters.

13. The process according to claim 1, wherein the length the reactor tubes are charged with oxidation catalyst to the length of 2.0 to 4.5 meters.

14. The process according to claim 1, wherein the length the reactor tubes are charged with oxidation catalyst to the length of 2.5 to 4.0 meters.

15. The process according to claim 1, wherein the internal diameter of each reactor tube is from 1.0 to 3.5 cm.

16. The process according to claim 1, wherein the internal diameter of each reactor tube is from 1.5 to 3.3 cm.

17. The process according to claim 1, wherein the internal diameter of each reactor tube is from 2.0 to 3.0 cm.

* * * * *